US008071599B2

(12) United States Patent
Wessel et al.

(10) Patent No.: US 8,071,599 B2
(45) Date of Patent: *Dec. 6, 2011

(54) METHODS OF TREATMENT OF CHRONIC PAIN USING ESZOPICLONE

(75) Inventors: Thomas Wessel, Lenox, MA (US); Judy Caron, Westwood, MA (US)

(73) Assignee: Sunovion Pharmaceuticals, Inc., Marlborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/838,554

(22) Filed: Jul. 19, 2010

(65) Prior Publication Data

US 2010/0280038 A1    Nov. 4, 2010

Related U.S. Application Data

(63) Continuation of application No. 11/099,078, filed on Apr. 5, 2005, now Pat. No. 7,776,858.

(60) Provisional application No. 60/559,590, filed on Apr. 5, 2004.

(51) Int. Cl.
*A61K 31/498* (2006.01)

(52) U.S. Cl. ....................................................... 514/249

(58) Field of Classification Search .................... 514/249
See application file for complete search history.

(56) References Cited

U.S. PATENT DOCUMENTS

| 5,786,357 | A | 7/1998 | Young et al. |
|---|---|---|---|
| 6,319,926 | B1 | 11/2001 | Cotrel et al. |
| 6,436,936 | B1 | 8/2002 | Young et al. |
| 6,444,673 | B1 | 9/2002 | Cotrel et al. |
| 6,864,257 | B2 | 3/2005 | Cotrel et al. |
| 7,125,874 | B2 | 10/2006 | Cotrel et al. |
| 7,381,724 | B2 | 6/2008 | Cotrel et al. |
| 7,465,729 | B2 | 12/2008 | Wessel et al. |
| 7,776,858 | B2 * | 8/2010 | Wessel et al. ................... 514/249 |
| 2005/0164987 | A1 | 7/2005 | Barberich |
| 2005/0176680 | A1 | 8/2005 | Lalji et al. |
| 2005/0215521 | A1 | 9/2005 | Lalji et al. |
| 2005/0267176 | A1 | 12/2005 | Barberich |
| 2007/0299055 | A1 | 12/2007 | Lalji et al. |
| 2008/0175903 | A1 | 7/2008 | Hopkins et al. |
| 2010/0004251 | A1 | 1/2010 | Barberich |

FOREIGN PATENT DOCUMENTS

| WO | WO9310787 | 6/1993 |
|---|---|---|
| WO | WO 2005060968 | 7/2005 |
| WO | WO 2005063248 | 7/2005 |
| WO | WO 2005063297 | 7/2005 |
| WO | WO 2005079851 | 9/2005 |
| WO | WO 2005097132 | 10/2005 |
| WO | WO 2008070000 | 6/2008 |

OTHER PUBLICATIONS

International Search Report and Written Opinion from corresponding International Application No. PCT/US2005/011593, mailed Dec. 23, 2005.

Affleck G, Urrows S, Tennen H, Higgins P, Abeles M, Seqeuntial daily relations of sleep, pain intensity, and attention to pain among women with fibromyalgia pain 68:363-368 (1996).

Asnis GM, Chakrabarty A, DuBoff EA, et al; Zolpidem for persistent insomnia in SSRI-treated depressed patients J Clin Psychiatry 60:668-676 (1999).

Barone P, Amboni M., Vitale C, Bonavita V., Treatment of nocturnal disturbance and excessive daytime sleepiness in Parkinson's disease, Neurology 63:S35-S38 (2004).

Benca RM, Ancoli-Israel A, Moldofsky H., Special considerations in insomnia diagnosis and management: Depressed, elderly, and chronic pain populations J Clin Psychiatry 65 (Suppl 8):26-35 (2004).

Billiard M, Bentley A. Is insomnia best categorized as a symptom or a disease? Sleep Medicine 5(Suppl 1):S35-S40 (2004).

Bliwise DL, Sleep disorders in Alzheimer's disease and other dementias, Clin. Cornerstone 6 Suppl 1A:S16-28 (2004).

Bloom BJ, Owens JA, McGuinn M, Nobile C., Shaeffer L, Alario AJ, Sleep and its relationship to pain, dysfunction, and disease activity in juvenile rheumatoid arthritis; J Rheumatol 29:169-173 (2002).

Bourguignon C, Labyak SE, Taibi D, Investigating sleep disturbances in adults with rheumatoid arthritis, Holist Nurs Pract 17:241-249 (2003).

Breslau N, Roth T, Rosenthal L, Andreski P, Sleep disturbance and psychiatric disorders: a longitudinal epidemiological study of young adults, Biol Psychiatry 39:411 418 (1996).

Chang PP, Ford DE, Mead LA et al., Insomnia in young men and subsequent depression. The Johns Hopkins Precursors Study, Am J Epidemiol. 146:105-114 (1997).

Dorsey CM, Lee KA, Scharf MB Effect of zolpidem on sleep in women with perimenopausal and postmenopausal insomnia: A 4-week, randomized, multicenter, double-blind placebo-controlled study Clin Ther 16:873-897 (2004).

Drewes AM Pain and sleep disturbances with special reference to fibromyalgia and rheumatoid arthritis, Rheumatology (Oxford) 38:1035-1038 (1999).

Drewes AM, Nielsen KD, Hansen B, Taagholt SJ, Bjerregard K, Svendsen L, A longitudinal study of clinical symptoms and sleep parameters in rheumatoid arthritis, Rheumatology (Oxford) 39:1287-1289 (2000).

Drewes AM, Svendsen L, Taagholt, Bjerregard k, Nielsen KD, Hansen B, Sleep in rheumatoid arthritis: a comparison with healthy subjects and studies of sleep/wake interactions, Br J Rheumatol 37:71-81 (1998).

Ford DE, Kamerow DB, Epidemiologic study of sleep disturbances and psychiatric disorders. An opportunity for prevention?, JAMA 262:1479-1484 (1989).

Ford DE, Cooper-Patrick L, Sleep disturbances and mood disorders:an epidemiologic perspective, Depress Anxiety 14:3-6 (2001).

Gillin JC, Are sleep disturbances risk factors for anxiety, depressive and addictive disorders? Acta Psychiatr Scand Suppl. 393:39-43 (1998).

Primary Examiner — Jennifer M Kim
(74) Attorney, Agent, or Firm — Heslin Rothenberg Farley & Mesiti P.C.

(57) ABSTRACT

The invention relates to the use of eszopiclone for the treatment of low-level, chronic pain and fatigue associated with pain.

4 Claims, No Drawings

OTHER PUBLICATIONS

Hyyppa MT, Kronholm E, Quality of sleep and chronic illnesses J Clin Epidemiol 42:633-638 (1989).

Katz DA, McHorney CA. Clinical correlates of insomnia in patients with chronic illness. Arch Intern Med 158:1099-1107 (1998).

Koren D, Arnon I, Lavie P, et al. Sleep complaints as early predictors of posttraumatic stress disorder: a 1-year prospective study of injured survivors of motor vehicle accidents. Am J Psychiatry 159:855-857 (2002).

Livingston G, Blizard B, Mann A, Does sleep disturbance predict depression in elderly people? A study in inner London, Br J Gen Pract. 43:445-448 (1993).

Londborg PD, Smith WT, Glaudin V, Painter Jr. Short-term cotherapy with clonazepam and fluoxetine: anxiety, sleep disturbance and core symptoms of depression., J. Affect Disord. 61:73-79 (2000).

Mahowald MW, Mahowald ML, Bundlie SR, Ytterberg SR, Sleep fragmentation in rheumatoid arthritis Arthritis Rheum 32:974-983 (1989).

McCall MV, A psychiatric perspective on insomnia, J Clin Psychiatry 62(Suppl 10):27 32 (2001).

McCurry SM, Ancoli-Israel S, Sleep dysfunction in Alzheimer's disease and other dementias Curr Treat Options Neurol 5:261-272 (2003).

Nierenberg AA, Keefe BR, Leslie VC et al, Residual symptoms in depressed patients who respond acutely to fluoxetine J Clin Psychiatry 60:221-225 (1999).

Nolen, WA, Hypnotics as concurrent medication in depression Jrnl of Affective Disorders 28 (1993) 179-188.

O'Bryant SE, Palav A, McCaffrey RJ, A review of symptoms commonly associated with menopause: implications for clinical neuropsychologists and other health care providers, Neuropsychol Rev. 13:145-152 (2003).

Perlis ML, Giles DE, Buysse DJ, et al. Self-reported sleep disturbance as a prodromal symptom in recurrent depression. J Affect Disord 42:209-212 (1997).

Punjabi NM, Shahar E, Redline S, et al, Investigators SHHS, Sleep-disordered breathing, glucose intolerance, and insulin resistance: the Sleep Heart Health Study Am J Epidemiol 160:521-530 (2004).

Renko A, Hiltunen L, Laakso M, et al. The relationship of glucose tolerance to sleep disorders and daytime sleepiness Diabetes Res Clin Pract 67:84-91 (2005).

Rickels K, Schweizer E, Case WG, DeMartinis N, Greenblatt DJ, Mandos LA, Espana FG. Nefazodone in major depression: adjunctive benzodiazepine therapy and tolerability, J, Clin Psychopharmacol 18:145-153 (1998).

Riemann D, Voderholzer U, Primary Insomnia: a risk factor to develop depression, J Affect Disord 76:255-259 (2003).

Shaver JL, Women and sleep, Nurse Clin North Am. 37:707-718 (2002).

Smith WT, Londborg PD, Glaudin V, Painter Jr. Shortterm augmentation of fluoxetine with clonazepam in the treatment of depression: a doub-blind study, Am J. Psychiatry 155:1339-1345 (1998).

Smith WT, Londborg PD, Glaudin V, Painter Jr. Summit Research Network. Is extended clonazepam cotherapy of fluoxetine effective for outpatients with major depression?, J Affect Disord 70:251-259 (2002).

Thorpy MJ, Sleep disorders in Parkinson's disease Clin Cornerstone 6 Suppl 1A:S7-15 (2004).

Tishler M, Barak Y, Paran D, Yaron M., Sleep disturbances, fibromyalgia and primary Sjogren's syndrome Clin Exp Rheumatol 15:71-74 (1997).

Van Cauter E, Polonsky KS, Scheen AJ, Roles of circadian rhythmicity and sleep in human glucose regulation Endocr Rev 18:716-738 (1997).

Walsh JK, Clinical and socioeconomic correlates of insomnia; J Clin Psychiatry 65 (Suppl 8):13-19 (2004).

Zamir G, Press J, Tal A, Tarasiuk A, Sleep fragmentation in children with juvenile rheumatoid arthritis J Rheumatol 25:1191-1197 (1998).

Furukawa et al., "Antidepressant and benzodiazepine for major depression," The Cochrane Collaboration®, pp. 1-43; (2005).

Furukawa et al., "Antidepressant and benzodiazepine for major depression," John Wiley & Sons, Ltd., (1), 1-43, (2005).

Cohen, et al.; "Sleep in chronic pain: problems and treatments," Intl Review of Psychiatry; vol. 12, No. 2: pp. 115-126 (2000).

Drewes, et al.; "Zopiclone as Night Medication in Rheumatoid Arthritis," Scand J Rheumatol; 27: 180-7 (1998).

PR Newswire Association LLC. Estorra™ PHase IIIB Insomnia Studies Underway in Subjects with Depression, Rheumatoid Arthritis and Perimenopause. PR Newswire, Dec. 18, 2003.

Gronblad et al. Effect of Zopiclone on Sleep Quality, Morning Stiffness, Widespread Tenderness and Pain and General Discomfort in Primary Fibromyalgia Patients. A Double-Blind Randomized Trial. Clinical Rheumatology, vol. 12, No. 2, 186-191 (1993).

Drewes et al. Zopiclone in the Treatment of Sleep Abnormalities in Fibromyalgia. Scan. J. of Rheumatology, vol. 20, No. 4, 288-293 (1991).

* cited by examiner

METHODS OF TREATMENT OF CHRONIC PAIN USING ESZOPICLONE

CROSS REFERENCE TO RELATED APPLICATIONS

This application is a continuation application of U.S. application Ser. No. 11/099,078, filed Apr. 5, 2005, which claims priority from U.S. provisional application 60/559,590, filed Apr. 5, 2004, the entire disclosures of which are incorporated herein by reference.

FIELD OF THE INVENTION

The invention relates to the use of eszopiclone for the treatment of chronic pain.

BACKGROUND OF THE INVENTION

Eszopiclone is a cyclopyrrolone that has the chemical name (+)6-(5-chloropyrid-2-yl)-5-(4-methylpiperazin-1-yl) carbonyloxy-7-oxo-6,7-dihydro-5H-pyrrolo[3-4-b]pyrazine or (+) 6-(5-chloro-2-pyridinyl)-6,7-dihydro-7-oxo-5H-pyrrolo[3,4-b]pyrazin-5-yl 4-methylpiperazine-1-carboxylate. The chemical structure of eszopiclone is shown below:

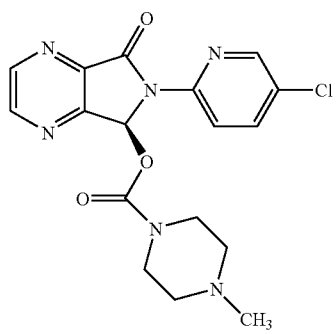

Eszopiclone is the S-(+)-optical isomer of the compound zopiclone, which is described in U.S. Pat. Nos. 6,319,926 and 6,444,673, and in Goa and Heel, [Drugs, 32:48-65 (1986)] and in U.S. Pat. Nos. 3,862,149 and 4,220,646. This isomer, which will hereinafter be referred to by its USAN-approved generic name, eszopiclone, includes the optically pure and the substantially optically pure (e.g., 90%, 95% or 99% optical purity) S-(+)-zopiclone isomer.

Zopiclone was the first of a chemically distinct class of hypnotic and anxiolytic compounds that offers a psychotherapeutic profile of efficacy and side effects similar to the benzodiazepines. This class of compounds, the cyclopyrrolones, appears to cause less residual sedation and less slowing of reaction times than the benzodiazepines, and it offers the promise of an improved therapeutic index over benzodiazepines.

The pharmacology of zopiclone has been shown both preclinically and clinically to be characterized by several elements. It is predominantly a hypnotic-sedative, offering significant activity on first treatment without concomitant respiratory or cardiac depression. The compound binds to the benzodiazepine receptor complex, or to a site linked closely to this receptor complex. (See Goa, K. L. and Heel, R. C. Drugs, 32:48-65, (1986); Brun, J. P., Pharmacology, Biochemistry and Behavior, 60 29:831-832, (1988); Julou, L. et at, Pharmacology, Biochemistry and Behavior, 23:653-659, (1985); Verma, A. and Snyder S. H., Ann. Rev. Pharmacol. Toxicol, 29:307-322, (1989). The central benzodiazepine receptor is a macromolecular complex that includes a site for the binding of gamma-aminobutyric acid (GABA), the inhibitory neurotransmitter, suggesting that benzodiazepines and chemically unrelated agonists including zopiclone may exert their effects by facilitating the synaptic effects of GABA. While it interacts with the benzodiazepine receptor, zopiclone apparently has minimal effects on memory, no interaction with alcohol, and little or no abuse or dependence potential. The drug is well absorbed from the stomach, and it is not highly bound to plasma proteins. The racemic mixture, zopiclone, has been in use for some years primarily as a hypnotic, and recently the USFDA approved use of eszopiclone (LUNESTRA™) for the treatment of insomnia.

SUMMARY OF THE INVENTION

The invention relates to methods of treating chronic pain with eszopiclone.

Thus, the invention relates to treating low-level, chronic pain comprising administering to a patient a therapeutically effective amount of eszopiclone.

DETAILED DESCRIPTION OF THE INVENTION

The invention relates to methods of treating chronic pain with eszopiclone. The S-(+)-zopiclone has an enantiomeric excess (e.e.) greater than 90%. It may be administered parenterally, transdermally or orally, preferably in an amount of 0.5 mg to 15 mg per day. In particular embodiments the eszopiclone is administered at 0.5 mg, 1.0 mg, 2.0 mg and 3.0 mg per day and in 0.5 mg, 1.0 mg, 2.0 mg and 3.0 mg per dosage.

It has now been discovered that eszopiclone is useful for treating low-level, chronic pain. While acute pain is a normal sensation triggered in the nervous system to alert an organism to possible injury, chronic pain persists. Pain signals keep firing in the nervous system for weeks, months, even years. There may have been an initial mishap—sprained back, serious infection, or there may be an ongoing cause of pain—arthritis, cancer, ear infection, but some people suffer chronic pain in the absence of any past injury or evidence of body damage. Many chronic pain conditions affect older adults. Common chronic pain complaints include headache, low back pain, cancer pain, arthritis pain, neurogenic or neuropathic pain (pain resulting from damage to the peripheral nerves or to the central nervous system itself), psychogenic pain (pain not due to past disease or injury or any visible sign of damage inside or outside the nervous system). The pain for which eszopiclone is best suited is neuropathic pain or pain associated with rheumatoid arthritis, osteoarthritis, muscle spasm, spasticity or fibromyalgia.

Neuropathic pain arises from disorders that include, but are not limited to, thoracic outlet obstruction syndromes, compression and entrapment neuropathies such as ulnar nerve palsy, carpel tunnel syndrome, peroneal nerve palsy, and radial nerve palsy; Guillain-Barré syndrome; pain associated with or resulting from: trauma caused by injury or surgical operation; tumors; bony hyperostosis; casts; crutches; prolonged cramped postures; hemorrhage into a nerve; exposure to cold or radiation; collagen-vascular disorders; metabolic disorders, such as diabetes, hypothyroidism, porphyria, sarcoidosis, amyloidosis, and uremia; infectious diseases such as Lyme disease and HIV; toxins, such as emetine, hexobarbital, barbital, chorobutanol, sulfonamides, phenyloin, nitrofurantoin, the vinca alkaloids, heavy metals, carbon monoxide, triorthocresylphosphate, orthodinitrophenol, and other solvents and industrial poisons; autoimmune reactions; nutritional deficiency, and vitamin B deficiency.

The effect of eszopiclone on pain may be direct, as a result of its action on benzodiazepine receptors, or indirect, as a result of its effect on sleep. The direct analgesic effects of eszopiclone were demonstrated in a clinical study presented in Example 1.

In a related aspect eszopiclone is useful for treating fatigue associated with pain.

The pharmacologic profile of hypnotic-sedative, anxiolytic agents of the benzodiazepine class has been rather well established (Goodman and Gilman: The Pharmacological Basis of Therapeutics, 7th. Edition, Chapt. 17, 340-351, (1985), MacMillan Publishing Co., N.Y.) and has been extended to non-benzodiazepine agents of the cyclopyrrolone class (Bardone, M. C. et al., Abstract No. 2319, 7th. Int. Congr. Pharm. Paris, July, 1978, Pergamon Press, London; Julou, L. et al., Pharmacology, Biochemistry and Behavior, 23:653-659 (1985)). Accordingly, a variety of experimental models, which are rather well characterized (Julou, L. et al., ibid, 1985) can be used to characterize the various activities of eszopiclone. The acute toxicity of a pharmaceutical composition comprising zopiclone can be determined in studies in which rats are administered at progressively higher doses (mg/kg) of pharmaceutical composition. That lethal dose which, when administered orally, causes death of 50% of the test animals, is reported as the $LD_{50}$.

To establish the safety of eszopiclone, a dose escalation study was carried out. Cardiovascular and respiratory parameters were evaluated in conscious dogs following acute intravenous administration of (R)-, (S)- or racemic zopiclone at three doses (3, 5 and 12 mg/kg). Blood gases and blood chemistries (pH, $pCO_2$, pO2, hematocrit, and lactate) remained unaffected in all dose groups. No evidence of cardiotoxicity, as evidence by the electrocardiogram (ECG), was observed following administration of racemic zopiclone or its enantiomers. Racemic zopiclone and eszopiclone produced dose dependent, transient decreases in blood pressure with an accompanying compensatory increase in heart rate, whereas (R) zopiclone had no effect. Administration of the highest dose (12 mg/kg) of racemic and (S)-zopiclone produced a more pronounced hypotensive effect (30-40% decrease from baseline). Complete recovery was not evident during the observational period. However, the values were returning toward baseline throughout the observation period. (R)-Zopiclone did not produce a consistent hemodynamic effect following 12 mg/kg.

Eszopiclone was evaluated for antimuscarinic activity in vivo. The racemate did not produce mydriasis in mice at any of the doses tested (maximum dose=100 mg/kg, p.o.). In another in vivo assay, neither (R)-, (S)-, nor racemic zopiclone significantly antagonized oxotremorine induced salivation in mice at doses up to 300 mg/kg, p.o. These results suggest that eszopiclone does not produce antimuscarinic effects and are consistent with eszopiclone's lack of in vitro affinity for muscarinic receptors.

All these studies point to little or no actions on the cardiovascular system or on the autonomic or peripheral nervous systems. Thus the drug appears to have a high safety margin with no indication of deleterious peripheral effects.

As used herein, and as would be understood by the person of skill in the medical art, to which the invention pertains, the recitation of the terms "eszopiclone" and "S-(+)-zopiclone" include pharmaceutically acceptable salts, hydrates, solvates, clathrates, and polymorphs of S-(+)-zopiclone. The term "pharmaceutically acceptable salt" refers to salts prepared from pharmaceutically acceptable non-toxic acids or bases including inorganic acids and bases and organic acids and bases. Salts may be prepared from pharmaceutically acceptable non-toxic acids including inorganic and organic acids. Suitable pharmaceutically acceptable acid addition salts for the compounds of the present invention include acetic, benzenesulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic, and the like. The term "solvate" refers to a compound—in this case eszopiclone—in the solid state, wherein molecules of a suitable solvent are incorporated in the crystal lattice. A suitable solvent for therapeutic administration is physiologically tolerable at the dosage administered. Examples of suitable solvents for therapeutic administration are ethanol and water. When water is the solvent, the solvate is referred to as a hydrate. In general, solvates are formed by dissolving the compound in the appropriate solvent and isolating the solvate by cooling or using an antisolvent. The solvate is typically dried or azeotroped under ambient conditions.

The term "preventing" as used herein refers to administering a medicament beforehand to forestall or obtund an attack. The person of ordinary skill in the medical art (to which the present method claims are directed) recognizes that the term "prevent" is not an absolute term. In the medical art it is understood to refer to the prophylactic administration of a drug to substantially diminish the likelihood or seriousness of a condition, and this is the sense intended in applicants' claims. The term "treating" includes prophylaxis as well as the amelioration of the acute symptoms. Note that "treating" refers to either or both of the amelioration of symptoms and the resolution of the underlying condition. In many of the conditions of the invention, the administration of eszopiclone may act not directly on the disease state, but rather on some pernicious symptom, and the improvement of that symptom leads to a general and desirable amelioration of the disease state.

As used herein, the recitation of the terms "eszopiclone" and "S-(+)-zopiclone" refers to eszopiclone having an enantiomeric excess (e.e.) greater than 90%. The term "enantiomeric excess" is well known in the art and is defined for a resolution of ab into a $$+b \text{ as } ee_a = \left(\frac{conc. \text{ of } a - conc. \text{ of } b}{conc. \text{ of } a + conc. \text{ of } b}\right) \times 100$$

The term "enantiomeric excess" is related to the older term "optical purity" in that both are measures of the same phenomenon. The value of ee will be a number from 0 to 100, zero being racemic and 100 being pure, single enantiomer. A compound which in the past might have been called 98% optically pure is now more precisely described as 96% ee.; in other words, a 90% e.e. reflects the presence of 95% of one enantiomer and 5% of the other in the material in question. In the case of eszopiclone, e.e. of greater than 95% is preferred; e.e. of greater than 98% is more preferred; and e.e. of greater than 99% is most preferred.

Racemic zopiclone is commercially available and can be made using various methods, such as those disclosed in U.S. Pat. Nos. 3,862,149 and 4,220,646. Eszopiclone is also commercially available or it may be prepared from racemic zopiclone using standard methods, such as chiral-phase chromatography, resolution of an optically active salt, stereoselective enzymatic catalysis by means of an appropriate microorganism, or asymmetric synthesis. U.S. Pat. No. 6,319,926 discloses methods for making (+) zopiclone, including resolution from racemic zopiclone by means of an optically active acid, such as D(+)-O,O'-dibenzoyltartaric acid.

Another method for making Eszopiclone is by synthesis from racemic zopiclone (or (RS)-zopiclone) by chemical resolution via the D-malate salt as shown in the following synthesis schematic.

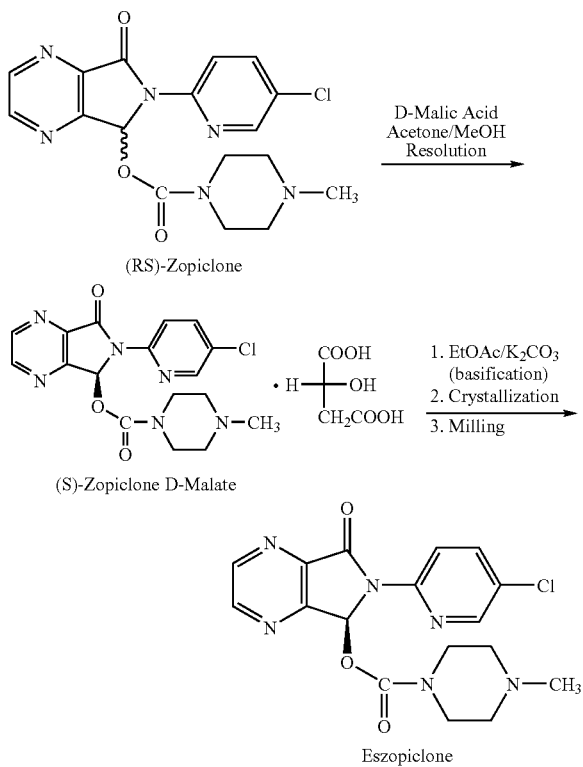

In the synthetic route shown above, (RS)-zopiclone and D-malic acid are dissolved in a mixture of acetone and methanol to form (S)-zopiclone D-malate and (R)-zopiclone D-malate. The two diastereomeric salts are resolved in-situ by selective crystallization, filtration and rinsing to produce highly (S)-enriched zopiclone D-malate salt. In this process, the majority of (R)-zopiclone D-malate remains in the mother liquors. In this method, the use of an acetone/methanol co-solvent system results in a highly diastereoselective salt crystallization, and preferably, the co-solvent ratio used should be in the range of approximately 1.9/1 to 2.3/1 w/w acetone in methanol. Preferably, this stage of the process may also include cooling the reaction mixture during the isolation step to a temperature in the inclusive range of about 10° C. to 15° C., and washing or rinsing the wet cake obtained after filtration with cold solvent, such as cold methanol.

The resulting (S)-zopiclone D-malate salt is converted to optically pure (S)-zopiclone free base by treatment with aqueous potassium carbonate and ethyl acetate, followed by phase separation and crystallization. In this process, once a solution of (S)-zopiclone free-base is obtained, additional enantiomeric enrichment (typically 1 to 4%) can be achieved by crystallization from ethyl acetate of low water content. The water content can be controlled, e.g., by azeotropic distillation, and incorporating an in-process control of water content into the crystallization process can further improve the robustness of enantiomeric purity. Preferably, the water level during this step is 2% or less, more preferably 1% or less, and most preferably 0.6% or less. The resulting optically pure eszopiclone free base can then be milled to a desired size for use as an active ingredient in a pharmaceutical composition according to the present invention. These compositions are useful in treating disorders that are affected by the binding of agonists to central nervous system and peripheral benzodiazepine receptors while avoiding the adverse effects associated with the administration of the racemic mixture of zopiclone.

The size of a prophylactic or therapeutic dose of eszopiclone in the acute or chronic management of disease will vary with the severity of the condition to be treated and the route of administration. The dose, and perhaps the dose frequency, will also vary according to the age, body weight, and response of the individual patient. In general, the total daily dose ranges, for the conditions described herein, is from about 0.5 mg to about 15 mg. Preferably, a daily dose range should be between about 0.5 mg to about 12.5 mg. Most preferably, a daily dose range should be between about 2.0 mg to about 10.0 mg. In managing the patient, the therapy may be initiated at a lower dose, perhaps about 0.5 mg to about 7.5 mg and increased up to about 10 mg or higher depending-on the patient's global response. It is further recommended that children and patients over 65 years, and those with impaired renal or hepatic function, initially receive low doses, and that they be titrated based on global response and blood level. It may be necessary to use dosages outside these ranges in some cases.

Pharmaceutical compositions of the present invention may be administered by any suitable route of administration that provides a patient with a therapeutically effective dosage of eszopiclone. Typically, the eszopiclone pharmaceutical compositions described herein will be formulated for oral administration or for inhalation. Suitable dosage forms include tablets, troches, cachets, caplets, capsules, including hard and soft gelatin capsules, and the like. Tablet forms, however, remain a preferred dosage form because of advantages afforded both the patient (e.g., accuracy of dosage, compactness, portability, blandness of taste and ease of administration) and to the manufacturer (e.g., simplicity and economy of preparation, stability and convenience in packaging, shipping and dispensing).

The pharmaceutical compositions may further include a "pharmaceutically acceptable inert carrier" and this expression is intended to include one or more inert excipients, which include starches, polyols, granulating agents, microcrystalline cellulose, diluents, lubricants, binders, disintegrating agents, and the like. If desired, tablet dosages of the disclosed compositions may be coated by standard aqueous or non-aqueous techniques. In one embodiment, coating with hydroxypropylmethylcellulose (HPMC) is employed. "Pharmaceutically acceptable carrier" also encompasses controlled release means. Compositions of the present invention may also optionally include other therapeutic ingredients, anti-caking agents, preservatives, sweetening agents, colorants, flavors, desiccants, plasticizers, dyes, and the like. However, any such optional ingredient must be compatible with eszopiclone to insure the stability of the formulation.

In the case where an oral composition is employed, a suitable dosage range for use is from about 0.5 mg to about 15.0 mg. Preferably, a dose range of between about 0.5 mg to about 12.5 mg is given as a once daily administration or in divided doses if required; most preferably, a dose range of from about 0.5 mg to about 10 mg is given, either as a once daily administration or in divided doses if required. Patients may be upward titrated from below to within this dose range to a satisfactory control of symptoms as appropriate.

Capsule Formulation

| ingredient | mg per capsule formulation A | mg per capsule formulation B | mg per capsule formulation C | mg per capsule formulation D |
|---|---|---|---|---|
| Eszopiclone | 0.5 | 1.0 | 2.0 | 3.0 |
| lactose | 79 | 78.5 | 77.5 | 76.5 |
| corn starch | 20 | 20 | 20 | 20 |
| magnesium stearate | 0.5 | 0.5 | 0.5 | 0.5 |
| total weight | 100 | 100 | 100 | 100 |

The active ingredient, eszopiclone, lactose, and corn starch are blended until uniform; then the magnesium stearate is blended into the resulting powder. The resulting mixture is encapsulated into suitably sized two-piece hard gelatin capsules.

Tablet Formulation

| ingredient | mg per tablet formulation A | mg per tablet formulation B | mg per tablet formulation C | mg per tablet formulation D |
|---|---|---|---|---|
| Eszopiclone | 0.5 | 1.0 | 2.0 | 3.0 |
| lactose | 153 | 152.5 | 151.5 | 150.5 |
| corn starch | 30 | 30 | 30 | 30 |
| pre-gelatinized corn starch | 15 | 15 | 15 | 15 |
| magnesium stearate | 1.5 | 1.5 | 1.5 | 1.5 |
| compression weight | 200 | 200 | 200 | 200 |

The active ingredient, eszopiclone, is sieved through a suitable sieve and blended with lactose, starch, and pregelatinized cornstarch. Suitable volumes of purified water are added and the powders are granulated. After drying, the granules are screened and blended with the magnesium stearate. The granules are then compressed into tablets using 7 mm diameter punches.

Tablets of other strengths may be prepared by altering the ratio of active ingredient to lactose or the compression weight and using punches to suit. In one embodiment, eszopiclone is formulated as film-coated tablets for oral administration containing the following inactive ingredients: calcium phosphate, colloidal silicon dioxide, croscarmellose sodium, hypromellose, lactose, magnesium stearate, microcrystalline cellulose, polyethylene glycol, titanium dioxide, triacetin and optionally FD&C Blue #2.

Example 1

Clinical Study on Treatment of Chronic Pain with Eszopiclone

The study was aimed at observing the effect of eszopiclone 3 mg compared to placebo on daytime function in subjects with insomnia related to rheumatoid arthritis. The study was a multicenter, randomized, double-blind, placebo controlled, parallel group study. The study had a one-week single-blind placebo run-in period, followed by four weeks of double blind treatment, and one week of single blind placebo washout.

A total of 153 subjects were randomized. Among them, 77 received 3 mg of eszopiclone (ESZ) nightly (at bedtime) for four weeks and 76 received matching placebo (PBO). The discontinuation rates were low, 5.2% in the ESZ group and 9.2% in the PBO group. The patient population was predominantly female (87%) and Caucasian (84%). Mean age was 52, with a range of 27-64. Subjects had a diagnosis of rheumatoid arthritis (as defined by the American College of Rheumatology) and were on stable doses of chronic rheumatoid arthritis medications for a minimum of 90 days prior to start of the single-blind placebo run-in period. In addition, subjects had insomnia symptoms including wake time after sleep onset (WASO) of $\geq 45$ minutes, and total sleep time $\leq 6.5$ hours. Diagnosis of rheumatoid arthritis predated the onset of insomnia symptoms.

During the double blind treatment, subjects were dosed with 3 mg eszopiclone (ESZ) or matching placebo (PBO) nightly (at bedtime) for four weeks. Data was analyzed with one-sided significance tests.

Eszopiclone had a significant effect on the change from baseline to end of study (Week 4) in the Overall score for the Arthritis Self-Efficacy Scale (the scale is made publicly available by Stanford Patient Education Research Center, 1000 Welch Road, Suite 204, Palo Alto, Calif. 94304). The Pain subscale had a statistically significant difference, both when analyzed alone or in combination with Other Symptoms. See Table 1.

TABLE 1

Arthritis Self-Efficacy Scale (Intent-to-Treat Population)

| Scale | Visit (Week) | Statistic | Placebo | | Eszopiclone 3 mg | |
|---|---|---|---|---|---|---|
| | | | Observed Value | Change from Baseline | Observed Value | Change from Baseline |
| Overall | 3 (Baseline) | N | 75 | | 77 | |
| | | Mean (SD) | 121.6 (39.8) | | 119.4 (40.9) | |
| | | 25th Percentile | 90.0 | | 88.0 | |
| | | Median | 124.0 | | 120.0 | |
| | | 75th Percentile | 156.0 | | 146.0 | |
| | | Minimum, Maximum | 36.0, 186.0 | | 34.0, 200.0 | |
| | 5 (Week 4) | N | 75 | 75 | 77 | 77 |
| | | Mean (SD) | 124.3 (39.7) | 2.7 (30.1) | 130.9 (38.2) | 11.5 (29.3) |
| | | 25th Percentile | 92.0 | −13.0 | 103.0 | −1.6 |
| | | Median | 131.0 | −1.0 | 132.6 | 12.0 |
| | | 75th Percentile | 160.0 | 19.0 | 162.5 | 26.0 |

TABLE 1-continued

Arthritis Self-Efficacy Scale (Intent-to-Treat Population)

| | | | Placebo | | Eszopiclone 3 mg | |
|---|---|---|---|---|---|---|
| Scale | Visit (Week) | Statistic | Observed Value | Change from Baseline | Observed Value | Change from Baseline |
| | | Minimum, Maximum | 38.0, 186.0 | −83.0, 83.0 | 27.0, 189.0 | −74.0, 124.0 |
| | | p-value vs. placebo [1] | | | 0.1593 | |
| | | Least Squares Means (SE) [2] | | 2.4 (3.2) | | 10.4 (3.2) |
| | | p-value vs. placebo [2] | | | | 0.0387 |
| | 6 (EOS) | N | 69 | 69 | 74 | 74 |
| | | Mean (SD) | 131.4 (37.3) | 9.0 (23.2) | 134.5 (35.9) | 14.0 (30.5) |
| | | 25th Percentile | 109.0 | −9.0 | 111.0 | −3.0 |
| | | Median | 135.0 | 3.0 | 133.0 | 12.5 |
| | | 75th Percentile | 160.0 | 23.0 | 163.0 | 32.0 |
| | | Minimum, Maximum | 44.0, 198.0 | −25.0, 94.0 | 50.0, 193.0 | −89.0, 84.0 |
| | | p-value vs. placebo [1] | | | 0.4285 | |
| | | Least Squares Means (SE) [2] | | 8.8 (2.9) | | 12.4 (2.9) |
| | | p-value vs. placebo [2] | | | | 0.1839 |
| Pain | 3 (Baseline) | N | 75 | | 77 | |
| | | Mean (SD) | 26.4 (9.6) | | 26.0 (11.5) | |
| | | 25th Percentile | 19.0 | | 17.0 | |
| | | Median | 26.0 | | 26.0 | |
| | | 75th Percentile | 33.0 | | 34.0 | |
| | | Minimum, Maximum | 7.0, 44.0 | | 8.0, 50.0 | |
| | 5 (Week 4) | N | 75 | 75 | 76 | 76 |
| | | Mean (SD) | 25.9 (9.7) | −0.4 (10.4) | 29.3 (9.9) | 3.3 (10.5) |
| | | 25th Percentile | 17.0 | −6.0 | 22.0 | −1.0 |
| | | Median | 26.0 | −1.0 | 28.0 | 3.0 |
| | | 75th Percentile | 33.0 | 5.0 | 38.0 | 10.5 |
| | | Minimum, Maximum | 8.0, 49.0 | −23.0, 34.0 | 8.0, 50.0 | −37.0, 30.0 |
| | | p-value vs. placebo [1] | | | 0.0150 | |
| | | Least Squares Means (SE) [2] | | −0.5 (1.0) | | 3.1 (1.0) |
| | | p-value vs. placebo [2] | | | | 0.0053 |
| | 6 (EOS) | N | 68 | 68 | 73 | 73 |
| | | Mean (SD) | 28.3 (9.4) | 2.1 (8.4) | 29.2 (9.8) | 2.7 (10.5) |
| | | 25th Percentile | 21.0 | −2.0 | 22.0 | −4.0 |
| | | Median | 27.0 | 1.0 | 30.0 | 2.0 |
| | | 75th Percentile | 35.0 | 5.0 | 37.0 | 8.0 |
| | | Minimum, Maximum | 8.0, 48.0 | −18.0, 32.0 | 9.0, 49.0 | −20.0, 35.0 |
| | | p-value vs. placebo [1] | | | 0.3489 | |
| | | Least Squares Means (SE) [2] | | 2.0 (1.0) | | 2.4 (0.9) |
| | | p-value vs. placebo [2] | | | | 0.3668 |
| Function | 3 (Baseline) | N | 75 | | 77 | |
| | | Mean (SD) | 58.9 (22.5) | | 57.2 (22.5) | |
| | | 25th Percentile | 42.0 | | 38.0 | |
| | | Median | 60.0 | | 59.0 | |
| | | 75th Percentile | 80.0 | | 77.0 | |
| | | Minimum, Maximum | 9.0, 90.0 | | 12.0, 90.0 | |
| | 5 (Week 4) | N | 75 | 75 | 76 | 76 |
| | | Mean (SD) | 61.0 (23.8) | 2.1 (14.3) | 62.0 (22.1) | 4.8 (15.7) |
| | | 25th Percentile | 42.0 | −7.0 | 45.5 | −1.0 |
| | | Median | 66.0 | 0.0 | 61.0 | 4.0 |
| | | 75th Percentile | 81.0 | 12.0 | 83.5 | 13.5 |
| | | Minimum, Maximum | 9.0, 90.0 | −33.0, 45.0 | 13.0, 90.0 | −34.0, 74.0 |
| | | p-value vs. placebo [1] | | | 0.4189 | |
| | | Least Squares Means (SE) [2] | | 1.9 (1.7) | | 4.2 (1.7) |
| | | p-value vs. placebo [2] | | | | 0.1697 |
| | 6 (EOS) | N | 68 | 68 | 73 | 73 |
| | | Mean (SD) | 63.8 (22.0) | 5.1 (11.1) | 64.1 (20.5) | 6.8 (15.6) |
| | | 25th Percentile | 51.0 | −1.0 | 45.0 | −1.0 |
| | | Median | 66.5 | 2.0 | 65.0 | 5.0 |
| | | 75th Percentile | 81.5 | 9.5 | 85.0 | 14.0 |
| | | Minimum, Maximum | 10.0, 90.0 | −21.0, 42.0 | 23.0, 90.0 | −45.0, 58.0 |
| | | p-value vs. placebo [1] | | | 0.5620 | |
| | | Least Squares Means (SE) [2] | | 5.0 (1.6) | | 6.2 (1.6) |
| | | p-value vs. placebo [2] | | | | 0.2909 |
| Other Symptoms | 3 (Baseline) | N | 73 | | 75 | |
| | | Mean (SD) | 36.9 (12.8) | | 36.2 (13.6) | |
| | | 25th Percentile | 27.0 | | 25.0 | |
| | | Median | 37.0 | | 37.0 | |
| | | 75th Percentile | 49.0 | | 49.0 | |
| | | Minimum, Maximum | 6.0, 58.0 | | 10.0, 60.0 | |
| | 5 (Week 4) | N | 73 | 71 | 76 | 74 |
| | | Mean (SD) | 37.4 (13.1) | 1.3 (11.5) | 39.3 (12.7) | 3.5 (10.5) |
| | | 25th Percentile | 28.0 | −5.0 | 31.5 | −2.0 |
| | | Median | 38.0 | 1.0 | 40.0 | 3.0 |
| | | 75th Percentile | 48.0 | 8.0 | 50.0 | 10.0 |

TABLE 1-continued

Arthritis Self-Efficacy Scale (Intent-to-Treat Population)

| Scale | Visit (Week) | Statistic | Placebo Observed Value | Placebo Change from Baseline | Eszopiclone 3 mg Observed Value | Eszopiclone 3 mg Change from Baseline |
|---|---|---|---|---|---|---|
| | | Minimum, Maximum | 11.0, 59.0 | −38.0, 36.0 | 6.0, 59.0 | −26.0, 41.0 |
| | | p-value vs. placebo [1] | | | 0.2044 | |
| | | Least Squares Means (SE) [2] | | 1.3 (1.2) | | 3.4 (1.2) |
| | | p-value vs. placebo [2] | | | | 0.1081 |
| | 6 (EOS) | N | 69 | 67 | 74 | 72 |
| | | Mean (SD) | 38.7 (11.7) | 1.2 (8.9) | 40.6 (12.6) | 3.8 (10.7) |
| | | 25th Percentile | 28.0 | −5.0 | 31.0 | −2.5 |
| | | Median | 40.0 | 1.0 | 41.5 | 3.0 |
| | | 75th Percentile | 47.0 | 5.0 | 51.0 | 10.0 |
| | | Minimum, Maximum | 17.0, 60.0 | −22.0, 25.0 | 8.0, 59.0 | −24.0, 39.0 |
| | | p-value vs. placebo [1] | | | 0.2733 | |
| | | Least Squares Means (SE) [2] | | 1.2 (1.1) | | 3.3 (1.1) |
| | | p-value vs. placebo [2] | | | | 0.0753 |
| Pain and Other Symptoms | 3 (Baseline) | N | 73 | | 75 | |
| | | Mean (SD) | 63.5 (20.7) | | 62.2 (22.6) | |
| | | 25th Percentile | 48.0 | | 47.0 | |
| | | Median | 65.0 | | 62.0 | |
| | | 75th Percentile | 79.0 | | 81.0 | |
| | | Minimum, Maximum | 21.0, 99.0 | | 19.0, 110.0 | |
| | 5 (Week 4) | N | 73 | 71 | 76 | 74 |
| | | Mean (SD) | 63.3 (20.5) | 1.0 (19.2) | 68.5 (21.1) | 6.9 (16.4) |
| | | 25th Percentile | 46.0 | −11.0 | 53.5 | 1.0 |
| | | Median | 64.0 | 0.0 | 69.7 | 6.0 |
| | | 75th Percentile | 79.0 | 10.0 | 86.0 | 13.0 |
| | | Minimum, Maximum | 25.0, 106.0 | −55.0, 55.0 | 14.0, 101.0 | −46.0, 50.0 |
| | | p-value vs. placebo [1] | | | 0.0681 | |
| | | Least Squares Means (SE) [2] | | 1.0 (1.9) | | 6.6 (1.9) |
| | | p-value vs. placebo [2] | | | | 0.0182 |
| | 6 (EOS) | N | 69 | 67 | 74 | 72 |
| | | Mean (SD) | 67.3 (19.7) | 3.4 (15.0) | 70.0 (21.0) | 7.0 (18.5) |
| | | 25th Percentile | 51.0 | −8.0 | 55.0 | −5.0 |
| | | Median | 64.0 | 2.0 | 71.0 | 7.5 |
| | | 75th Percentile | 83.0 | 12.0 | 88.0 | 17.0 |
| | | Minimum, Maximum | 31.0, 108.0 | −28.0, 52.0 | 27.0, 107.0 | −44.0, 52.7 |
| | | p-value vs. placebo [1] | | | 0.3068 | |
| | | Least Squares Means (SE) [2] | | 3.2 (1.8) | | 6.1 (1.8) |
| | | p-value vs. placebo [2] | | | | 0.1317 |

[1] The pairwise comparison is a one-sided test performed using an ANOVA model, using the MIXED procedure with treatment and site as fixed effects.
[2] The pairwise comparison is a one-sided test performed using an ANCOVA model, using the MIXED procedure, with treatment and site as fixed effects and baseline as the covariate.

Eszopiclone also had a significant effect on change from baseline to the end of study in the Subject Pain Severity Assessment. See Table 2.

TABLE 2

Subject Pain Severity Assessment (Intent-to-Treat Population)

| Visit (Week) | Statistic | Placebo Observed Value | Placebo Change from Baseline | Eszopiclone 3 mg Observed Value | Eszopiclone 3 mg Change from Baseline |
|---|---|---|---|---|---|
| 3 (Baseline) | N | 73 | | 76 | |
| | Mean (SD) | 4.9 (2.4) | | 5.1 (2.3) | |
| | 25th Percentile | 3.0 | | 3.0 | |
| | Median | 5.0 | | 5.0 | |
| | 75th Percentile | 7.0 | | 7.0 | |
| | Minimum, Maximum | 0.0, 10.0 | | 0.0, 10.0 | |
| 5 (Week 4) | N | 74 | 73 | 76 | 76 |
| | Mean (SD) | 5.1 (2.7) | 0.3 (2.1) | 4.6 (2.7) | −0.5 (2.6) |
| | 25th Percentile | 3.0 | −1.0 | 2.5 | −2.0 |
| | Median | 6.0 | 0.0 | 5.0 | −1.0 |
| | 75th Percentile | 7.0 | 1.0 | 7.0 | 0.5 |

TABLE 2-continued

Subject Pain Severity Assessment (Intent-to-Treat Population)

| | | Placebo | | Eszopiclone 3 mg | |
|---|---|---|---|---|---|
| Visit (Week) | Statistic | Observed Value | Change from Baseline | Observed Value | Change from Baseline |
| | Minimum, Maximum | 1.0, 10.0 | −6.0, 6.0 | 0.0, 10.0 | −7.0, 7.0 |
| | p-value vs. placebo [1] | | | 0.1121 | |
| | Least Squares Means (SE) [2] | | 0.2 (0.3) | | −0.5 (0.2) |
| | p-value vs. placebo [2] | | | | 0.0228 |

[1] The pairwise comparison is a one-sided test performed using an ANOVA model, using the MIXED procedure with treatment and site as fixed effects.
[2] The pairwise comparison is a one-sided test performed using an ANCOVA model, using the MIXED procedure, with treatment and site as fixed effects and baseline as the covariate.

The pain assessment was made by subjects in response to a question "How much pain have you had because of your illness in the past week?" The severity of pain was rated by each subject on a scale from 0 to 10 with no pain at value of 0 and severe pain at value of 10.

The contents of each of the references cited herein, including the contents of the references cited within the primary references, are herein incorporated by reference in their entirety. The invention being thus described, it is apparent that the same can be varied in many ways. Such variations are not to be regarded as a departure from the spirit and scope of the present invention, and all such modifications and equivalents as would be obvious to one skilled in the art are intended to be included within the scope of the following claims.

The invention claimed is:

1. A method for treating pain in a patient suffering from pain associated with fibromyalgia, the method comprising administering to the patient a therapeutically effective amount of eszopiclone having an enantiomeric excess greater than 90%.

2. A method according to claim 1, wherein the therapeutically effective amount of eszopiclone is administered parenterally, transdermally, orally or by inhalation.

3. A method according to claim 1, wherein the therapeutically effective amount of eszopiclone is administered in an amount of 0.5 mg to 15 mg per day.

4. A method according to claim 3, wherein the therapeutically effective amount of eszopiclone is administered in an amount chosen from 0.5 mg, 1.0 mg, 2.0 mg, and 3.0 mg per dosage.

* * * * *

UNITED STATES PATENT AND TRADEMARK OFFICE
CERTIFICATE OF CORRECTION

| | | |
|---|---|---|
| PATENT NO. | : 8,071,599 B2 | Page 1 of 1 |
| APPLICATION NO. | : 12/838554 | |
| DATED | : December 6, 2011 | |
| INVENTOR(S) | : Wessel et al. | |

It is certified that error appears in the above-identified patent and that said Letters Patent is hereby corrected as shown below:

On the title page item (73): Delete "Sunovion Pharmaceuticals, Inc."

and insert -- Sunovion Pharmaceuticals Inc. --

Signed and Sealed this
Seventh Day of February, 2012

David J. Kappos
*Director of the United States Patent and Trademark Office*